United States Patent
Maiser et al.

(10) Patent No.: US 10,894,991 B2
(45) Date of Patent: Jan. 19, 2021

(54) VALIDATION OF CONTINUOUS VIRAL CLEARANCE

(71) Applicant: Bayer Aktiengesellschaft, Leverkusen (DE)

(72) Inventors: Benjamin Maiser, Leverkusen (DE); Peter Schwan, Leverkusen (DE); Laura David, Leverkusen (DE); Martin Lobedann, Cologne (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 16/343,125

(22) PCT Filed: Oct. 20, 2017

(86) PCT No.: PCT/US2017/057298
§ 371 (c)(1),
(2) Date: Apr. 18, 2019

(87) PCT Pub. No.: WO2018/075716
PCT Pub. Date: Apr. 26, 2018

(65) Prior Publication Data
US 2019/0316213 A1     Oct. 17, 2019

(30) Foreign Application Priority Data
Oct. 21, 2016  (EP) .................................. 16194959

(51) Int. Cl.
*C12Q 1/70*  (2006.01)
(52) U.S. Cl.
CPC .................... *C12Q 1/701* (2013.01)
(58) Field of Classification Search
None
See application file for complete search history.

(56) References Cited

FOREIGN PATENT DOCUMENTS

| | | |
|---|---|---|
| AU | 2014100888 A4 | 9/2014 |
| EP | 2377927 A1 | 10/2011 |

OTHER PUBLICATIONS

Bae et al., Kor J Microbiol. Biotechnicol., vol. 37, No. 4, pp. 377-382 (Year: 2009).*
Klutz et al., Chemical Engineering and Processing: Process Intensification, vol. 102, pp. 88-102 (Year: 2016).*
PCT International Search Report for PCT/US2017/057298, dated Jan. 30, 2018.
Bae, et al., "Evaluation of Viral Inactivation Efficacy of a Continuous Flow Ultraviolet-C Reactor (UVivatec)," Kor. J. Microbial. Biotechnol., (2009), vol. 37, No. 4: 377-382.
Lutz, Herb, "Inline spiking for viral clearance validation of continuous processes," in "Integrated Continuous Biomanufacturing II", Chetan Goudar, Amgen Inc. Suzanne Farid, University College London Christopher Hwang, Genzyme-Sanofi Karol Lacki, Novo Nordisk Eds, ECI Symposium Series, (2015). http://dc.engconfintl.org/biomanufact_ii/97.
Klutz, et al., "Continuous viral inactivation at low pH value in antibody manufacturing," Chemical Engineering and Processing, (2015), vol. 102: 88-101.
Cameron, et al., "Virus clearance methods applied in bioprocessing operations: an overview of selected inactivation and removal methods," Pharmaceutical Bioprocessing, (2014), vol. 2, No. 1: 75-83.
Aranha, et al., "Viral Clearance Strategies for Biopharmaceutical Safety, Part II: A Multifaceted Approach to Process Validation," Pharmaceutical Technology, (2001), 26-42.
Klutz, et al., "Developing the biofacility of the future based on continuous processing and single-use technology," Journal of Biotechnology, (2015), vol. 213: 120-130.
Klutz, et al., "Narrow residence time distribution in tubular reactor concept for Reynolds number range of 10-100," Chemical Engineering Research and Design, (2015), vol. 95: 22-33.

* cited by examiner

*Primary Examiner* — Shanon A. Foley
*Assistant Examiner* — Myron G Hill
(74) *Attorney, Agent, or Firm* — McBee Moore & Vanik IP, LLC

(57) ABSTRACT

Disclosed herein is a method for validation of continuous viral clearance comprising the steps of providing a probe to be validated, spiking the probe in a valid manner, performing viral clearance, sampling the spiked probe and analyzing the sample of the spiked probe of step d).

7 Claims, 6 Drawing Sheets

VALIDATION OF CONTINUOUS VIRAL CLEARANCE

CROSS-REFERENCE TO RELATED APPLICATIONS

This application is the National Stage entry of International Application No. PCT/US2017/057298, filed 19 Oct. 2017, which claims priority to European Patent Application No. 16194959.9, filed Oct. 21, 2016.

BACKGROUND

Field

Description of Related Art

Continuous processing for the production of therapeutic proteins gains more and more importance and first solutions for realization of truly continuous systems are emerging. An essential part of a continuous process for the production of therapeutic proteins is the viral inactivation. Klutz et al. introduced the coiled flow inverter (CFI) as a tool for continuous low pH viral inactivation (Klutz, S. et al. 2015, *Journal of Biotechnology* 213, pp. 120-130). It offers tight and defined residence time distributions to adapt the batch concept for continuous processes (Klutz, S. et al. (2015) *Chemical Engineering Research and Design* 95, pp. 22-33). Additionally, continuous processes for the production of therapeutic protein allowing the use of single use technology are especially interesting.

However, in order to use continuous processing for the production of therapeutic proteins according to guidelines and standards such as GMP (ICH harmonised tripartite guideline) the FDA (CBER, 2/28/1997 guideline) and the EMEA (CPMP/BWP/268/95, 1996 guideline or EMEA/CHMP/BWP/398498, 2009 guideline) it not only needs to be ensured that any viral contamination is reliably removed, but this also has to be demonstrated.

Hence, viral clearance testing is required by regulatory authorities for investigational new drug (IND) submission and it is especially critical in process development for inter alia antibodies (monoclonals), recombinant proteins and glycoproteins as well as tissue and blood-derived products.

In other words, effective viral clearance is mandatory for all biopharmaceutical production processes to guarantee patients' safety. For the production of monoclonal antibodies (mAb) for example, two orthogonal dedicated viral clearance steps are necessary. Each step has to reach a log reduction value (LRV)≥4.

SUMMARY

It was therefore an object of the present invention to provide a novel, simple and inexpensive solution for demonstrating that viral contamination is reliably cleared, i.e. removed or inactivated.

The invention achieves this object by provision of a method for validation of continuous viral clearance comprising the steps of:
a) providing a probe to be validated,
b) spiking the probe in a valid manner,
c) performing viral clearance,
d) sampling the spiked probe, and
e) analyzing the sample of the spiked probe of step d).

DETAILED DESCRIPTION OF A PREFERRED EMBODIMENT

Figure 1:
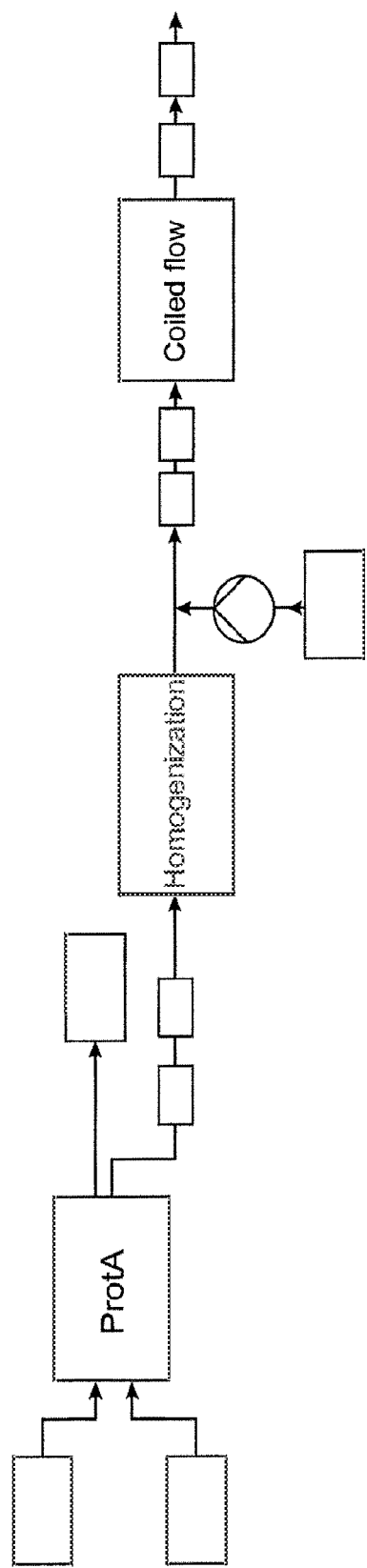
FIGS. 1-6 depict embodiments as described herein.

This method has the advantage that it allows for a simple and inexpensive validation of continuous viral clearance.

As used herein the term "validation" refers to the process of establishing evidence or a high degree of assurance that a specific process, method, or system will consistently produce a result meeting pre-determined acceptance criteria.

In the pharmaceutical industry, for example, it is very important to assure that the process adapted to produce itself will consistently produce the expected results.

As used herein the term "continuous" refers to the fact that the validation is carried out continuously as the probe is processed. In contrast in a "batch" method, a complete charge of a probe, e.g. a product, would be validated at a given time point. In other words, a continuous process as used herein refers to a process for carrying out at least two process steps in series, whereby the second process step starts processing the probe before the first process step is completed.

As used herein the term "clearance" refers to the removal of viral particles or inactivation of viral particles.

Thus, the step of performing viral clearance results in less viral particles being present in the probe and/or the viral particles are no longer capable of infecting cells especially host cells, i.e. they are inactivated.

As used herein the term "probe" refers to a substance potentially containing viruses.

As used herein the term "spiking" refers to deliberately increasing the amount of viral load substantially.

As used herein the term "virus" is used interchangeably with the term "viral particle" and refers to an agent that is smaller than a bacterium and that can only reproduce after infecting a host cell.

In many cases of viral clearance studies the concentration of viruses in a given sample is extremely low. In other extraction processes, low levels of impurity may be negligible, but because viruses are infective impurities, even one viral particle may be enough to ruin an entire process chain. It is for this reason that special measures must be taken to determine the appropriate removal or inactivation method for whatever type of virus is being extracted from whatever type of probe.

Spiking studies were created specifically for this purpose. A spiking study is a study done in order to determine the possible methods of viral removal, i.e. clearance or inactivation. They rely on the principle that increasing the viral count (or level of activity) of a probe by a factor of $10^4$ or $10^5$ of the original will only change the virus removal/inactivation ratios by one order of magnitude. From this knowledge, spiking studies known in the state of the art have been created in which the virus number (or level of activation) is increased or "spiked" by a factor of $10^4$ or $10^5$ of the original probe. A probe with this new high number or level of activity is then typically subjected to the clearance method of choice. In the state of the art the viral count or level of activity is taken at the beginning and at the end of the clearance method of choice and used in the calculation of Reduction Factor. This reduction factor (RF) of conventional studies for a virus removal or inactivation step is calculated using the following equation:

$$RF_{step} = \log_{10}[(V1 \times T1)/(V2 \times T2)]$$

Where:
V1=volume of spiked feedstock prior to the clearance step;
T1=virus concentration of spiked feedstock prior to the clearance step;
V2=volume of material after the clearance step; and
T2=virus concentration of material after the clearance step.

As used herein the term "valid manner" refers to the fact that the spiking needs to be carried out reproducibly and the desired level of viral particle load has to be always ensured.

In other words, it has to be ensured that the spiking point is chosen in such a manner that the viral particle load consistently reaches the desired level independently of the unit operation prior to viral clearance.

Hence, the viral clearance method needs to take the special features of a continuous process into account, e.g. varying pH levels, residence time, temperature, additive concentrations, homogeneity of the solution and conductivity.

In one embodiment of the method for validation the probe is a stream and/or a product stream.

As used herein the term "stream" refers to a continuous flow of liquid and/or gas.

As used herein the term "product stream" refers to a stream comprising a product.

In one embodiment of the method for validation described herein the probe is a product stream. This product stream for example flows from one unit operation to another unit operation until the product has reached the desired characteristics.

In an alternative embodiment of the method for validation described herein the probe is a stream. This stream may for example be a stream entering a production process.

The same production process may comprise both the method for validation described herein, wherein the probe is a product stream and the method for validation described herein wherein the probe is a stream.

The reduction factor needed for a certain stream and/or a product stream is dependent on many different factors, some of which include:
the expected initial concentration of virus, and/or
the product being purified, and/or
the infective dose of the virus (for in vivo usage), and/or
whether inactivation is a viable alternative to complete removal, and if this is the case the inactivation conditions.

For adding the spiking material a pump or a syringe can be used.

In a preferred embodiment of the method for validation described herein the step of spiking the probe in a valid manner is carried out using a connector e.g. a Y junction and/or a T junction.

In a preferred embodiment of the method for validation described herein no mixing unit is used to mix the stream and/or product stream and the spiking material.

In an alternative embodiment a static mixer and/or a mixing vessel or vessel without mixing is used to mix the stream and/or product stream and the spiking material.

In one embodiment of the method for validation described herein the step d) of sampling the spiked probe comprises sampling for a predetermined period of time.

This embodiment is advantageous as in takes into account that in a continuous production process the product stream can be subject to periodically fluctuating conditions in different unit operations e.g. with regard to the pH value, conductivity or product concentration.

The advantage of this embodiment becomes especially clear when referring to the example described below. In this example the product stream is an eluate of a continuous chromatography and a coiled flow inverter (CFI) is used for viral inactivation. In this embodiment the sampling for predetermined period of time i.e. a fixed sampling duration has the effect that influences of the fluctuating pH resulting from the continuous chromatography are excluded. In this preferred embodiment it is moreover preferred, that the sampling duration is set to one switch time.

As used herein the term "switch time" refers to the time in which the continuous chromatography elutes a specific column before switching to the next column for elution"

Via setting the sampling duration to one switch time, the complete collection of the expected pH levels resulting from the continuous chromatography is collected. In other words, via sampling over a predetermined period of time, e.g. a switch time, the periodically fluctuating conditions are taken into account. Otherwise—for example in the case of pH measurements following a continuous chromatography—the result may be falsified or not reproducible depending on whether a sample is taken at a moment in time when the product stream leaving the continuous chromatography is at a high pH level compared to a moment in time when the product stream leaving the continuous chromatography is at a low pH level.

Thus, in order to provide a method which reliably gives the same result under the same conditions, i.e. which is suited for a validation procedure for continuous viral inactivation, it is preferred that the step of sampling the spiked probe comprises sampling for a predetermined period of time, e.g. a switch time, whenever the unit operation preceding the viral inactivation has periodically fluctuating conditions.

In one embodiment of the method for validation described herein the probe comprises at least one component selected from the group consisting of a peptide, protein, a small molecule drug, a nucleic acid.

As used herein the term "peptide" refers to a polymer of amino acids of relatively short length (e.g. less than 50 amino acids). The polymer may be linear or branched, it may comprise modified amino acids, and it may be interrupted by non-amino acids. The term also encompasses an amino acid polymer that has been modified; for example, by disulfide bond formation, glycosylation, lipidation, acetylation, phosphorylation, or any other manipulation, such as conjugation with a labeling component, such as but not limited to, fluorescent markers, particles, biotin, beads, proteins, radioactive labels, chemiluminescent tags, bioluminescent labels, and the like.

As used herein the term "protein" refers to a polypeptide of amino acids. The term encompasses proteins that may be full-length, wild-type, or fragments thereof. The protein may be human, non-human, and an artificial or chemical mimetic of a corresponding naturally occurring amino acid, as well as to naturally occurring amino acid polymers and non-naturally occurring amino acid polymer.

Preferably the protein is a therapeutic protein.

As used herein the term "therapeutic protein" refers to a protein that can be administered to an organism to elicit a biological or medical response of a tissue, an organ or a system of said organism.

Even more preferably the protein is an antibody.

The term "antibody" as used herein refers to a binding molecule such as an immunoglobulin or immunologically active portion of an immunoglobulin, i.e., a molecule that contains an antigen-binding site.

As used herein the term "small molecule drug" refers to a low molecular weight (<900 daltons) compound that may help regulate a biological process.

As used herein, the term "nucleic acid" refers to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated.

In the example described below a coiled flow inverter (CFI) was used for viral inactivation. It was constructed to deliver a defined minimum residence time.

As used herein the term "minimum residence time" refers to the time which a single virus/viral particle at least remains in a given device, e.g. the CFI.

In one embodiment of the method for validation described herein the step of spiking the sample in a valid manner comprises spiking the sample after homogenization.

As used herein the term "homogenization" refers to a unit operation which ensures that the one or more characteristics of the probe that is important for viral clearance is consistent within the probe.

For example, if the probe is a product stream, the unit operation prior to viral clearance is a continuous chromatography and the characteristic of the probe that is important for viral clearance is a pH value the homogenization ensures that the entire product stream when leaving the homogenization is at the same pH level.

In a preferred embodiment the homogenization is conducted in a homogenization loop.

As used herein the term "homogenization loop" refers to a continuous stirred tank reactor (CSTR) constructed from tubing. In other words, the homogenization loop does not consist of one large tank with a stirring device but rather of an circular arrangement of tubings through which the stream is pumped. Since the internal volume flow is higher than the inlet and outlet flow, a good mixing of the incoming stream is achieved.

When using a homogenization loop as a continuous stirred tank reactor (CSTR) in order to adjust the pH level of the continuous chromatography, which fluctuates between pH 3 and pH 7, it is impossible to identify from which concrete chromatography column a given sample originates. Therefore, the sampled volume could hold the eluate of one or even two unspecified columns of the continuous chromatography system. In order to exclude the influence of different chromatography columns, some sample points within the CFI were sampled twice.

In the example discussed below the spiking point was set after the homogenization loop.

This was the case since the CFI was the actual low pH viral inactivation device. Therefore, a spiking before the homogenization loop would have caused a potential loss in maximum LRV because the probe has a certain residence time at low pH levels in the homogenization loop before the actual Unit Operation (UO) i.e. the low pH viral inactivation in the CFI.

In an embodiment of the method for validation described herein the viral clearance of step c) is a viral inactivation.

This viral inactivation is preferably carried out at a pH level ≤4. Viral inactivation at these conditions has the effect that given a suitable residence time it reliably inactivates large enveloped viruses.

In an embodiment of the method for validation described herein the viral clearance of step c)

the viral clearance is a viral inactivation, which is carried out in a coiled flow inverter (CFI).

This viral inactivation is for example carried out at a pH level ≤4 in a CFI. Using the CFI is advantageous since it ensures that the residence time needed for viral inactivation is reliable and reducibly ensured.

Preferably, the viral inactivation is carried out at a pH level ≤4.

However, viral inactivation may also be achieved using solvents and/or detergents such as tri(n-butyl)phosphate and Tween or Triton X-100 or other inactivating chemicals such as iodine or beta-propiolactone. In addition viral inactivation using the CFI may also be achieved via irradiation and/or precipitation, e.g. using caprylic acid.

Moreover, a combination of viral inactivation via low pH treatment and using solvents and/or detergents and/or irradiation and/or precipitation may be employed.

In a further embodiment of the method for validation described herein the viral clearance of step c) is carried out in a plugged flow reactor, a straight tube and/or a straight helix in addition or instead of a CFI.

In yet another embodiment of the method for validation described herein the step of sampling the spiked probe comprises back to front sampling.

As used herein the term "back to front sampling" refers to a method in which sampling is started at the end of a process and then progresses towards the start of said process.

For example, in the case of viral inactivation in the CFI back to front sampling means that the first samples are taken at or near the outlet of the CFI, then sampling progresses towards the inlet of the CFI, i.e. against current flow in the CFI.

In case of viral inactivation as continuous process back to front sampling has the advantage that the stream or the product stream does not have to be stopped in order to take a sample at the start of the continuous process. In case of the example described below such a pause of the continuous product stream would distort the analysis as viral inactivation would continue at the low pH value of ≤4 but the product stream would not progress through the CFI. Hence, the level of viral inactivation would no longer correlate with the distance that the product stream has progressed in the CFI. In addition, the required part of the CFI would have to be flushed and reaching the steady state initially after every sampling, leading to widely increased experiment durations.

Moreover, sampling within the CFI leads to a disturbance of the internal flow patterns. Therefore, the sampling method had to be chosen carefully in order to guarantee valid results also for this reason. Thus, in the example described below sampling was started at XM18 and ending with XM12 (cf. FIG. 3).

In yet another embodiment of the method for validation described herein the step of sampling the spiked probe comprises immediately neutralizing each probe drop when it enters a sampling container.

The feature of immediately neutralizing each probe drop when it enters a sampling container, can be achieved via filling the container with a buffer that immediately shifts the pH value to ~pH 7, for example 2 M Tris buffer. Thus, it is ensured that in cases of viral inactivation using low pH values, which is highly time-dependent the reaction is reliably stopped upon sampling, thereby preventing inhomogeneous residence times at low pH levels within the samples.

Preferably samples are taken via threeway stopcocks. Moreover any method of withdrawing a sample may be used which allows to take samples without interrupting the process, e.g. T junctions may be used or the tube of the CFI may be successively shortened.

In yet another embodiment of the method for validation described herein the step d) analyzing the sample of the spiked probe comprises determination whether viral particles are present.

This determination can be carried out via and method that allows the increase in numbers of viral particles and their determination for example using standard methods known in the art such as next generating sequences and/or other PCR-based methods in combination with sequencing methods.

In a further embodiment of the method for validation described herein step d)—analyzing the sample of the spiked probe—comprises quantification of the viral particles.

In general, virus quantification involves counting the number of viruses in a specific volume to determine the virus concentration via methods such as plaques assay, focus forming assay, endpoint titration—also termed endpoint dilution assay—protein-based virus quantification assays, transmission electron microscopy, tunable resistive pulse sensing, quantitative PCR and/or large volume plating.

Preferably said quantification of viral particles is achieved via endpoint titration and/or large volume plating.

Endpoint titration—also termed endpoint dilution assay—quantifies the amount of virus required to kill 50% of infected hosts or to produce a cytopathic effect in 50% of inoculated tissue culture cells. Thus, it relates to the tissue culture Infective dose (TCID50) as the measure of infectious virus titer. When used in the context of tissue culture, host cells are plated and serial dilutions of the virus are added. After incubation, the percentage of cell death (i.e. infected cells) is manually observed and recorded for each virus dilution, and results are used to mathematically calculate a TCID50 result. Two methods commonly used to calculate TCID50 are the Spearman-Karber and the Reed-Muench method.

Large volume plating (LVP) refers to the same method of detection as the $TCID_{50}$ assay. In contrast to endpoint titration, a much larger amount of liquid is used for LVP, leading to a much lower limit of detection.

Even more preferably said quantification of viral particles is achieved via a combination of endpoint titration and large volume plating.

Preferably the cleared virus is a large enveloped viruses. Moreover, it is possible to clear small non-enveloped viruses via virus filters.

Preferably for carrying out the method for validation described herein single-use equipment is employed.

Preferably for carrying out the method for validation described herein disposable equipment is employed.

In a preferred embodiment the equipment is single-use and disposable

In a different aspect the present invention relates to the use of the method for validation described herein in a continuous process for the production of therapeutic proteins.

Thus, overall the method for validation described herein for the first time overcomes the prejudice in the state of the art that viral clearance should be carried out in a batch process in order to ensure a defined residence time.

Moreover, the method for validation described herein demonstrates for the first time that it is possible to
- transfer a defined batch residence time to a continuous process,
- assure a valid spiking procedure in a continuous process,
- carry out the validation at process conditions without disturbing the process itself via choosing a valid spiking point,
- sample representative samples while taking all fluctuations and measurement difficulties into account, e.g. fluctuation of pumps, pH, virus concentration, concentration fluctuations, measurement of the stream conditions,
- create a valid sampling procedure without disturbing later sampling points.

Example

Below an exemplary method for carrying out a validation of continuous viral clearance is described.

For all experiments a prototype of a Tarpon Biosystems BioSMB chromatography unit was used. The analytics of all experiments included pH and conductivity measurement with the help of pH electrodes and single-use luer conductivity sensors, respectively, as well as assays for virus concentration determination.

Moreover, a coiled flow inverter (CFI) was used for viral inactivation. It was constructed to deliver a minimum residence time of 120 min. Therefore, the average residence time is higher than 120 min and was determined by RTD (residence time distribution) characterization as described below. A picture of the final CFI setup can be seen in FIG. 3.

The overall plant setup can be seen in FIG. 1. In this setting the low pH viral inactivation step is placed after the chromatography unit. The elution profile of the Tarpon BioSMB chromatography unit shows a periodically fluctuating pH level between the elution buffer (pH 3.1) and the wash buffer (pH 7.0). As the overall pH for low pH viral inactivation should lie below 4, a homogenization loop is realized for equalizing of the pH profile. In other words, the homogenization loop (HL) can be understood as a continuous stirred tank reactor (CSTR) leading to pH levels constantly below 4. After the HL, the actual low pH viral inactivation takes place within the coiled flow inverter (CFI).

In order to characterize the two unit operations HL and CFI, residence time distribution studies were performed. The change in conductivity between MilliQ water and 1M NaCl solution was measured. In detail, the flow rate was set to 4.8 mL/min. The step functions were performed with the help of a three-way stopcock. Three different setups were investigated: the HL (A), the CFI (B) and the combination of HL and CFI (C). The step functions were performed in both possible directions. Therefore, after the complete filling with 1 M NaCl solution, the experiment was repeated in the other direction by filling the UO, i.e. the CFI or the HL with MilliQ water at constant flux of 4.8 mL/min. The concentration measurements were normalized to 1 and limited to values between 0.5% and 99.5% of the maximum value. The average residence time was determined by numerical integration using the trapezoidal rule. The residence time was then normalized to one with the help of the average residence time. The relative width $R_W$ was calculated according to equation 1. $\Theta_{0.005}$ and $\Theta_{00.995}$ hereby represent the dimensionless time points were 0.5% and 99.5% of the maximum dimensionless concentration is reached. The relative width therefore shows how narrow the RTD is.

$$R_W = \frac{\theta_{0.005}}{\theta_{0.995}} \quad (1)$$

Two different continuous chromatography methods were tested in order to investigate two different average pH levels for the low pH viral inactivation. The experimental procedure for both methods was the same. In detail, the CFI was started and CIPed (cleaned in place) independently from the chromatography. Before the first virus experiment, the CFI was completely flushed with buffer and CIPed with 0.1 M NaOH solution. Afterwards, another buffer flush was performed, leaving the whole system without air bubbles trapped inside. In parallel, the continuous chromatography was started, which needed 2.5 h of initial run before the first column went through all cycles once. The HL and CFI system were connected to the continuous chromatography during the initial phase after flushing and CIP procedure. After the first 2.5 h of continuous chromatography the CFI had to fill completely with spiked chromatography eluate for 3 h in order to reach the steady state. The necessary duration of 3 h was determined from the corresponding RTD experiments. After the first virus experiment, the CFI was CIPed with 5 M NaOH for at least 1 h.

A novel spiking procedure for a continuous process had to be developed. In order to achieve the standard spiking level of 5%, 230 μL/min spiking material had to be added to the 4.6 mL/min chromatography eluate stream. A Gilson Minipuls 3 pump was used to add the spike stream to the chromatography eluate stream via a connector. No internal mixing unit was used. The spiking point was set after the homogenization loop.

In order to withdraw samples from different time points within the CFI, three-way stopcocks were introduced between certain frames. The sampling points as well as the final CFI can be seen in FIG. 3. The time points which are represented by the different sampling points were determined by measuring the average residence time within the complete CFI. As the low pH viral inactivation is highly time-dependent, the reaction had to be stopped during the sampling procedure. Therefore, each sampling container was filled with 4.13 mL of 2 M Tris buffer prior to sampling. With the help of this method, the pH of each drop of sample was neutralized immediately when entering the sampling container. This prevented inhomogeneous residence times at low pH levels within the samples.

In order to exclude influences of the fluctuating pH, the sampling duration was set to one switch time (17.3 min) of the continuous chromatography. This leads to a complete collection of the expected pH levels from the continuous chromatography.

When using a homogenization loop as a continuous stirred tank reactor (CSTR) in order to adjust the pH level of the continuous chromatography, which fluctuates between pH 3 and pH 7, it is impossible to identify from which concrete chromatography column a given sample taking in the CFI originates. Therefore, the sampled volume could hold the eluate of one or even two unspecified columns of the continuous chromatography system. In order to exclude the influence of different chromatography columns, some sample points within the CFI have were sampled twice. The first sample was taken within one switch time (17.3 min). Afterwards, the sampling was paused for half a switch time (8.65 min) before the sampling was continued for another switch time. Within the pausing of sampling, the three-way stopcock position was not changed. The continuing flow through the sample point was fed into a waste container. With this procedure, no residual fluid was trapped within the sampling system. Residual fluid would be exposed to low pH levels for a prolonged residence time and therefore falsify the results.

With the help of the results of the water and NaCl solution experiments performed in order to characterize the used homogenization loop (HL) and coiled flow inverter (CFI) the corresponding residence times to the sampling points were determined. The results of the RTD measurements can be seen in FIG. 4.

As mentioned above the CFI was designed to deliver a minimum residence time of 120 min.

Prior to the performed experiments, cytotoxicity and interference assays were performed. The necessary final dilution of the sample was determined to be 1:54. With this dilution factor, no effect on cell growth and virus replication could be observed.

The pH and conductivity measurements of both continuous chromatography modes show a periodically fluctuating behavior. Moreover, a dampening effect of the HL as well as partly of the CFI can be seen.

FIG. 1 shows a schematic overview of a process scheme for a pre-viral study.

Figure 2:
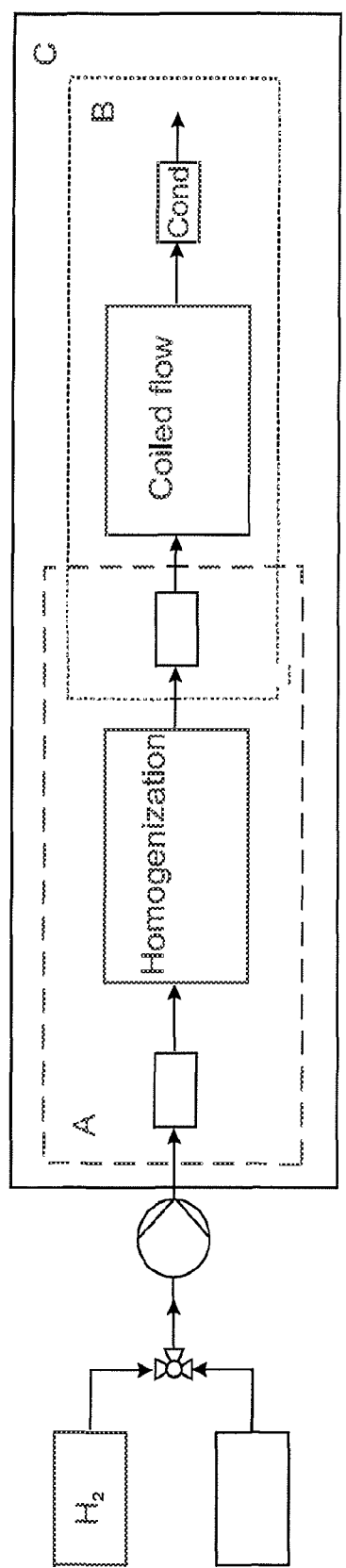

FIG. 2 shows the experimental setup for RTD measurements

Figure 3:
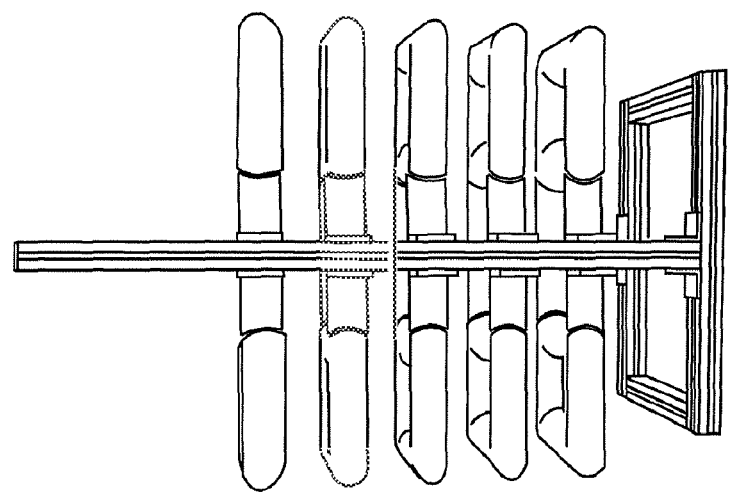
Figure 3:
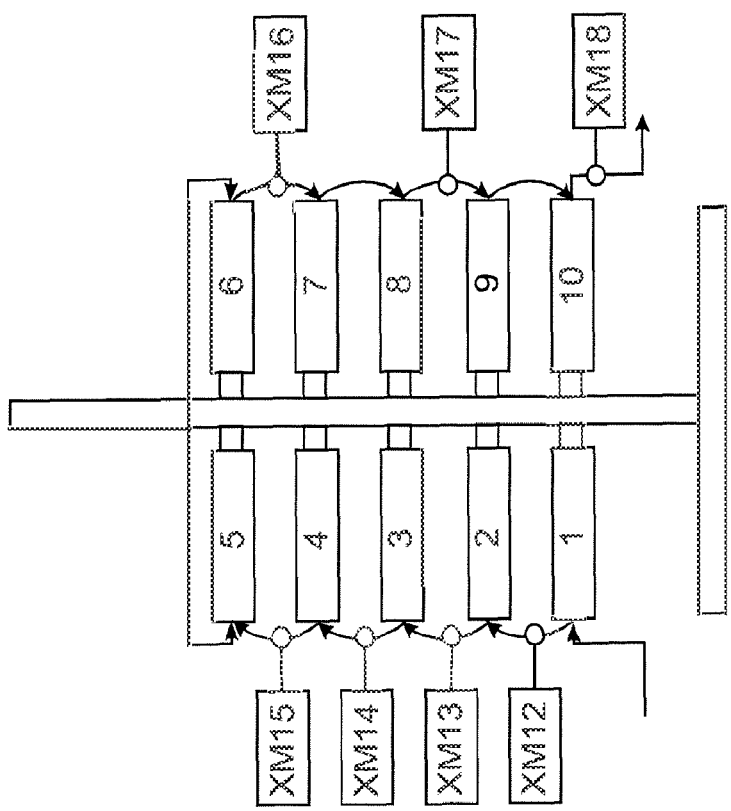

Cond=conductivity sensor, Setup A for RTD measurements of HL, Setup B for RTD measurements of CFI, Setup C for RTD measurements of both UO together FIG. 3 shows a schematic overview of the sampling points as well as the final CFI.

Figure 4:
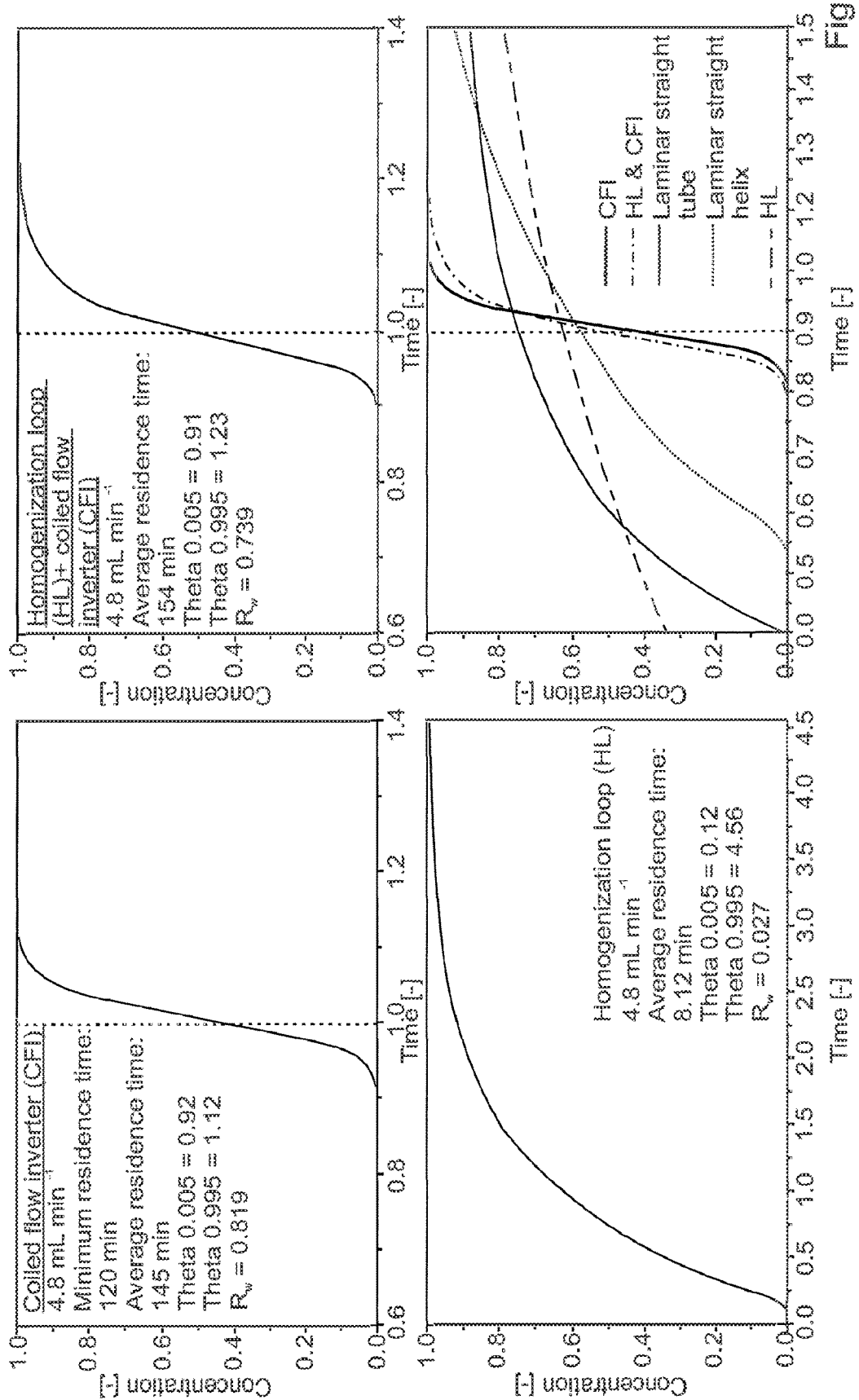

FIG. 4 depicts the results of the residence time distribution characterization The upper left diagram of FIG. 4 shows the RTD characterization results for the CFI. The average residence time was determined at 145 min with a relative width $R_W$ of 0.819. Consequently, every arm out of the 10 arms realized within the CFI provides a residence time of 14.5 min. The RTD within the CFI is very narrow, leading to a minimized residence time of every single fluid element, i.e. viral particle.

The lower left diagram of FIG. 4 shows the results for the HL. It shows the typical CSTR RTD behavior. The average residence time are 8.12 min, the $R_W$ is 0.027. The upper right diagram FIG. 4 shows the measurement for the combination of HL and CFI. In comparison to the CFI results shown in the upper left diagram, the average residence time increases to 154 min, the relative width decreases to 0.739. The lower right diagram FIG. 4 shows the overall comparison of the experimental results as well as calculated graphs for laminar straight tubes and laminar straight helixes. The combination of HL and CFI leads to a visibly wider residence time distribution than using solely the CFI. Nevertheless, both constellations show a significantly better RTD than the alternatives, the laminar straight tube and the laminar straight helix.

Figure 5:
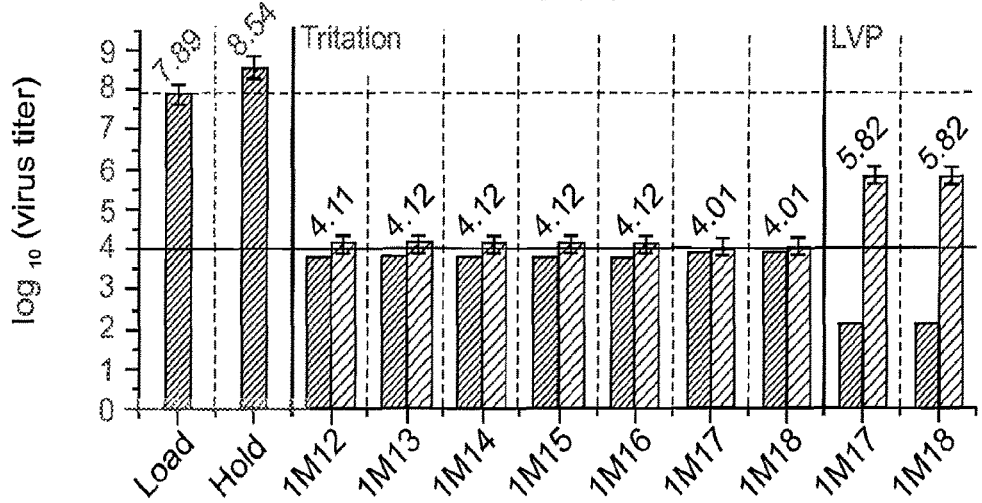
Figure 5:
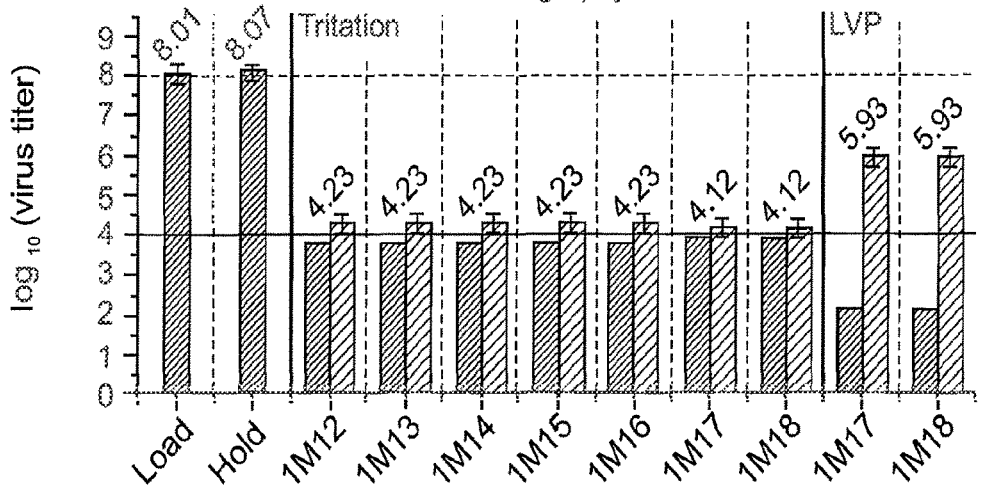
Figure 5:
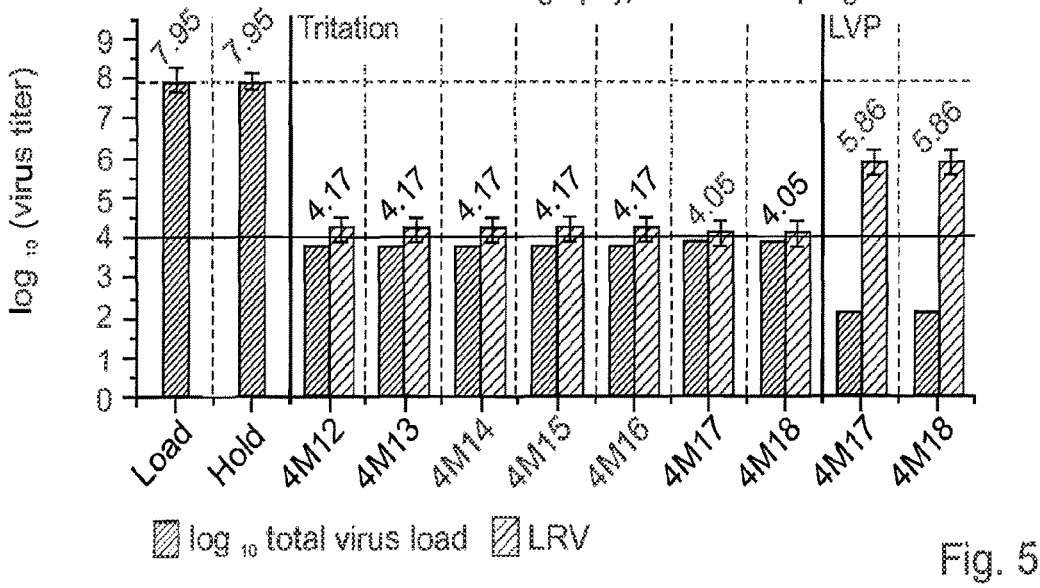

FIG. 5 depicts the results of the pre-viral study continuous process

The virus titer and LRV results of two experiments can be seen in FI. 5. The upper part of the diagram shows the results of the single sampling with mode A of continuous chromatography. The first two columns represent the virus titer results for the load and hold sample. As no decrease in virus titer can be seen for the hold sample, process conditions (e.g. temperature and buffer composition) as well as the test item itself (mAB) have no influence on the virus stability. Therefore, the viral inactivation is solely caused by the low pH conditions. The columns in the middle of the diagram show virus titer and corresponding LRV values from the titration samples. The virus titer in all samples were reduced down to the limit of detection, leading to ">" LRV values. The LRV reduction from 4.12 (1M16) to 4.01 at samples 1M17 and 1M18 is caused by different dilution factors since samples 1M17 and 1M18 were additionally analyzed via large volume plating. Therefore, the analyzed volumes are changing from 33.33 µL (1M16) to 44.44 µL (1M17 and 1M18). On the right hand side of the diagram the LVP results from sample 1M17 and 1M18 can be seen. Even with an analyzed volume of 2133.33 µL no infected wells could be found, leading to LRV values of >5.82.

The middle and the lower diagram of FIG. 5. show the results of the two samplings with mode B of ProtA chromatography. The sampling procedure was started with 3M18 for 17.31 min. After a pause of 8.66 min, sample 4M18 was drawn. The further sampling was done pair wise as well.

Figure 6:
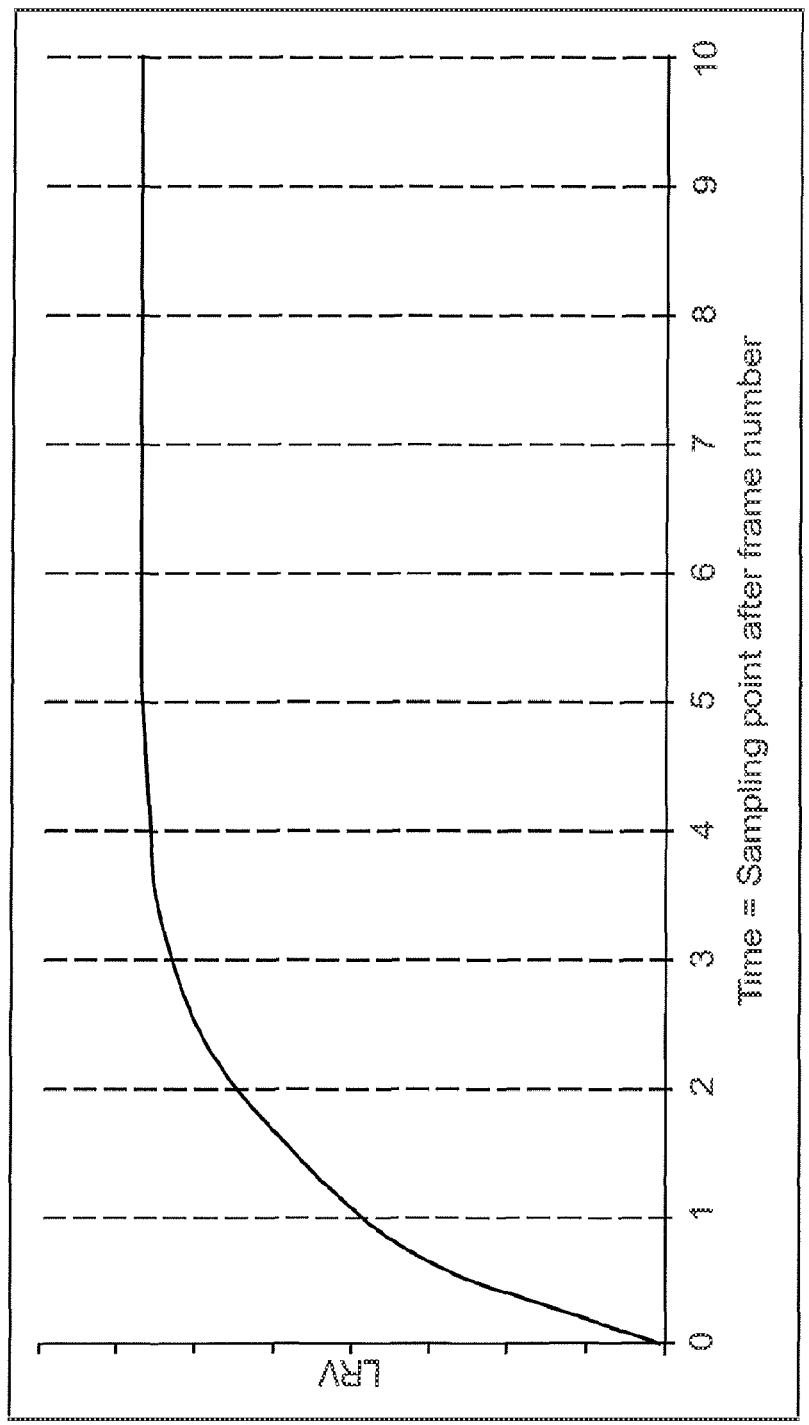

FIG. 6 shows a schematic diagram of the log reduction value (LRV) of viral titer against the residence time in the CFI, which in the case of the CFI is equal to a specific location in the CFI. In other words, a given log reduction of viral titer is always achieved at the same location within the CFI due to the reaction kinetics in the CFI. Hence, the LRV at a given time point 1 will always respond to said LRV at the specific sampling point within the CFI e.g. in this case the sampling point after frame 1. Likewise, in this example the LRV at time point 6 will always correspond to the LRV at the sampling point after frame 6. Therefore, sampling of the spiked probe is location specific rather than time point specific as it would be the case under batch conditions.

REFERENCES

Klutz, S.; Magnus, J.; Lobedann, M; Schwan, P.; Maiser, B.; Niklas, J.; Temming, M; Schembecker, G. (2015): *Developing the biofacility of the future based on continuous processing and single-use technology. In Journal of Biotechnology* 213, pp. 120-130

Klutz, S.; Kurt, S. K.; Lobedann, M; Kockmann, N (2015): *Narrow residence time distribution in tubular reactor concept for Reynolds number range 10-100. In Chemical Engineering Research and Design* 95, pp. 22-33

The invention claimed is:

1. A method for assessing and validating continuous viral clearance via viral inactivation at a pH level ≤4, comprising
    a) providing a stream or a product stream from a continuous chromatography process to be assessed and validated, wherein the stream or product stream has already passed through a chromatography unit operation in the continuous chromatography process,
    b) spiking the stream or product stream in a valid manner to ensure the spiking is carried out reproducibly and that a desired level of viral particle load is always reached,
    c) performing viral clearance via viral inactivation at a pH level ≤4,
    d) sampling the spiked stream or product stream for a switch time of the chromatography unit operation, wherein sampling comprises:
        sampling the spiked stream or product stream in a back to front sampling, and by using a buffer, immediately neutralizing the pH value of each spiked stream or product stream drop to ~pH 7 when the spiked stream or product stream enters a sampling container to ensure the viral clearance step is reliably stopped upon sampling, and
    e) analyzing the sample of the spiked probe of step d) to quantify viral particles in order to validate and determine viral clearance.

2. The method according to claim 1, further comprising step a1) performing homogenization after step a) and before step b).

3. The method according to claim 1, wherein in c) the viral clearance is a viral inactivation which is carried out in a coiled flow inverter (CFI).

4. The method according to claim 1, wherein e) analyzing the sample of the spiked stream or product stream comprises determination whether viral particles are present.

5. The method according to claim 1 in a continuous process for the production of therapeutic proteins in vitro.

6. The method according to claim 2, wherein step a1) performing homogenization ensures that the stream or product stream when leaving the homogenization is at the same pH level.

7. The method according to claim 2, wherein the homogenization is conducted in a homogenization loop.

* * * * *